United States Patent [19]

Park et al.

[11] 4,053,506

[45] Oct. 11, 1977

[54] PRODUCTION OF FIBER-GRADE TEREPHTHALIC ACID

[75] Inventors: Chang-Man Park, Naperville, Ill.; Donald G. Micklewright, Broadview Heights, Ohio

[73] Assignee: Standard Oil Company (Indiana), Chicago, Ill.

[21] Appl. No.: 574,035

[22] Filed: May 2, 1975

[51] Int. Cl.$^2$ ............................................. C07C 51/42
[52] U.S. Cl. .................................................... 260/525
[58] Field of Search ......................................... 260/525

[56] References Cited

U.S. PATENT DOCUMENTS

| | | | |
|---|---|---|---|
| 3,210,416 | 10/1965 | Fragen et al. | 260/525 |
| 3,683,018 | 8/1972 | Longland | 260/525 |
| 3,853,924 | 12/1974 | Meyer et al. | 260/525 |

*Primary Examiner* — James O. Thomas, Jr.
*Assistant Examiner* — A. Siegel
*Attorney, Agent, or Firm* — Fred R. Ahlers; Arthur G. Gilkes; William T. McClain

[57] ABSTRACT

Terephthalic acid (TA) or isophthalic acid (IA) of fiber-grade quality is recovered under oxidation temperature and pressure conditions from fluid oxidation effluent from catalytic liquid phase oxidation of the respective xylene isomer in acetic acid with molecular oxygen by crystal size classification and acetic acid mother liquor displacement with hot, fresh acetic acid followed by quenching the new suspension of phthalic acid crystals in said hot solvent with colder fresh acetic acid solvent and separating the product crystals. Such technique eliminates the need for separately purifying crude TA or IA or converting TA or IA to the respective dimethyl ester and purifying the ester.

7 Claims, 1 Drawing Figure

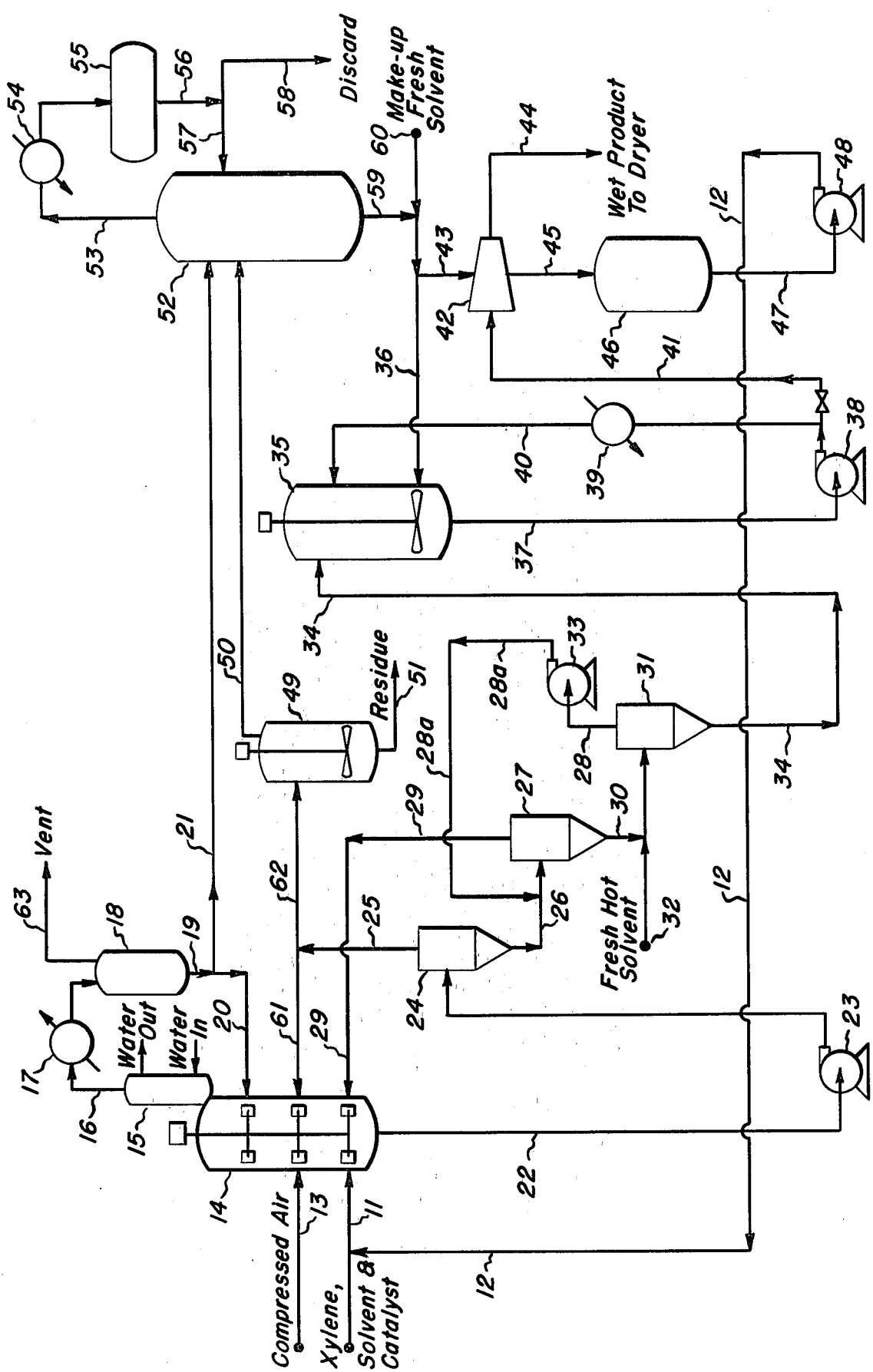

PRODUCTION OF FIBER-GRADE TEREPHTHALIC ACID

BACKGROUND OF THE INVENTION

High molecular weight polyesters of the Dacron, Terylene, and Kodel type, Vycron fibers, and Mylar film have long heretofore been prepared as described in U.S. Pat. No. 2,465,319 by transesterification of dimethyl terephthalate with the appropriate glycol followed by polycondensation. Such transesterificiation has been preferred over direct esterification of terephthalic acid (TA) with glycol by reason of the exceptionally high purity requirements imposed on the reactants for polyester production and the commercial unavailability of fiber-grade quality TA. Since the commercial availability in late 1965 of fiber-grade quality TA product from a unique TA purification process, such product has rapidly replaced dimethyl terephthalate as reactant with glycol in polyester manufacture.

Commercially produced TA from p-xylene oxidation at the present time contains approximately 0.2% impurities. A major impurity is formylbenzoic acid, an intermediate product in the oxidation of p-xylene. Lesser amounts of unidentified color forming precursors and color bodies having the benzil, flurenone, or anthroquenone structure are also present. Fiber-grade TA purity requirements of greater than 99.9% pure have been found essential for direct reaction with glycol because of the subsequent reactions and heating employed in the formation of polymeric materials. Such attendant impurities either interfere with the subsequent formation of the linear polyesters by producing lower melting products or form dark colored impurities or impurities which impart dark colors to the polyester product.

The direct esterification of TA with glycol or alkylene oxide is known to have manifest economic advantages as compared to the indirect transesterification route, however, there remains the problem of obtaining TA of fiber-grade quality direct from p-xylene oxidation.

To solve this problem, the present invention provides a unique route for recovering high purity TA from the fluid effluent of the catalytic liquid phase oxidation of p-xylene in acetic acid solvent. In addition, high purity IA or other aromatic acids also of limited solubility in acetic acid can be provided by this process.

BRIEF SUMMARY OF THE INVENTION

The present invention comprises a unique recovery of high purity terephthalic acid (TA), isophthalic acid (IA), or mixtures thereof from the oxidation of the appropriate dialkyl substituted benzene, under later specified oxidation conditions, with molecular oxygen in the presence of acetic acid solvent containing a heavy metals oxidation catalyst and a source of bromine. The unique recovery is based on the fact that phthalic acids of limited acetic acid solubility exist at oxidation temperature and pressure as high purity crystals suspended in an acetic acid solution of catalyst components and aforementioned impurities. In the generally applied TA and/or IA recovery technique, the fluid oxidation effluent is cooled to a temperature at or below the boiling point of the acetic acid component of the effluent at atmospheric pressure. During the cooling, further crystallization of TA and/or IA occurs as well as growth of crystal nucleii. Accompanying this further crystallization and crystal growth is the rejection of impurities from solution resulting in occlusion of such rejected impurities within the TA and/or IA crystalline product. Based on these facts, recovery of high purity product is accomplished in the present invention by subjecting said fluid effluent to a classification system operated at or about oxidation temperature and pressure and using therein fresh, hot acetic acid to displace substantially all of the original liquid portion of the oxidation effluent containing impurities and also small phthalic acid crystals. A new suspension of larger crystals in the hot, fresh acetic acid is formed in the classification-displacement step. The new suspension of large crystalline phthalic acid is next quenched preferably by admixture with cold, fresh acetic acid in an amount sufficient so that the remaining impurities will be retained in solution at atmospheric pressure and a temperature at or below the boiling point of fresh acetic acid. After depressuring the cooled, diluted new suspension of large phthalic acid crystals, crystalline phthalic acid product is separated from the fresh acetic acid at atmospheric pressure by suitable solid-liquid separation. The separated, fresh acetic acid is recycled to the reaction zone and the separated wet crystalline product is dried.

BRIEF DESCRIPTION OF THE DRAWING

The accompanying drawing is a schematic flow sheet illustrating the conduct of catalytic liquid phase oxidation in reactor 14, condensation of overhead vapors in primary condensor 15 and secondary condensor 18, displacement at or about reaction temperature of substantially all of the liquid oxidation effluent with hot, fresh acetic acid in hydroclones 24, 27, and 31, quenching the hot crystalline slurry with cold, fresh acetic acid in reslurry drum 35, solid-liquid separation by centrifuge 42, collection of fresh acetic acid in drum 46, flash evaporation of a substantial portion of the displaced original oxidation effluent in flash drum 49, and recovery of fresh solvent in column 52. Also shown are pressure control valves, transfer lines, and pumps needed to move the various suspensions of phthalic acid through the system.

This drawing illustrates one embodiment of the conduct of the present invention and a detailed description of such specific embodiment will be given later with reference to this drawing.

DETAILED DESCRIPTION OF THE DRAWING AND INVENTIVE PROCESS

In practicing the invention, optimum oxidation conditions are employed so that a high purity oxidation product of fiber-grade is crystallized out under the reaction conditions followed by a careful separation technique which minimizes contamination of the high purity crystals with intermediates, by-products, or color bodies.

A meta or para dialkyl substituted benzene of at least 99% purity having an alkyl substituent consisting of 1 to 4 carbon atoms, e.g. p-xylene, is oxidized with molecular oxygen, as from compressed air, in the presence of an acetic acid solution of one or more heavy metals oxidation catalysts and a source of bromine. The xylene feed and catalyst enter the oxidation zone through line 11 after being combined with recycled solvent from line 12. Compressed air enters the oxidation zone through line 13. The oxidation is conducted continuously in a single stirred-tank reactor (STR) 14. Experimental evidence has shown that contamination of phthalic acid crystals with impurities is directly proportional to the initial concentration of these components in the mother liquor. A single stage STR is preferred over a series of STR's or a plug flow reactor because the level of intermediate and by-product concentrations are lower while nucleation and growth of crystals is taking place in the single stage STR.

A weight ratio of acetic acid solvent to dialkylbenzene in the range of 3.0–10.0:1.0, preferably 4.0–8.0:1.0, is provided in the STR by premixing fresh solvent, dialkylbenzene and recycled mother liquor from recovery of high purity product before being fed to the STR. Such ratio of solvent to dialkylbenzene has been found to decrease impurity by preventing an oxygen starved situation from occurring.

Water concentration in the reactor is effectively controlled by removing a portion of the reactor overhead condensate which is rich in water. Vapors from the STR pass through primary water cooled reflux condensor 15 which condenses and removes, as liquid reflux to STR 14, a large portion of the acetic acid contained in the overhead vapor. Uncondensed vapors pass through line 16 and heat exchanger 17 wherein more vapor is condensed and condensate is collected in a secondary condensor pot 18. Remaining vapor is vented to the atmosphere through line 63 while condensate is removed from secondary condensor pot 18 through line 19. Part of condensate stream 19 containing water rich acetic acid is returned to the oxidation zone through line 20 and part of the water rich stream is passed to solvent recovery through line 21. By maintaining lower water concentration, e.g. 5–10%, in the reaction solvent, catalyst activity is increased, further diminishing impurity formation.

Molecular oxygen is supplied in excess of the theoretical requirement, such excess being evidenced by oxygen concentration in reactor 14 exhaust gas (acetic acid free basis) of 3% or greater, preferably greater than 5 volume %, but below the explosive limit of 8%. As previously mentioned, the formation of color bodies and intermediates is inhibited by avoiding an oxygen starved reaction medium in the foregoing manner. Recompression (not shown) of substantially solvent free reactor exhaust gas in line 63 from the reactor and recycle thereof after oxygen enrichment can provide an economic advantage.

The catalyst system employed is the fundamental system known from U.S. Pat. No. 2,833,816. Cobalt and/or manganese are the preferred catalyst metals and may be dissolved in solvent as the metals or in ionic form or as components of an organic compound and preferably are in the form of acetates or acetate hydrates which are soluble in the reaction solvent. The bromine component of the catalysis is supplied by a substance capable of affording bromine at reaction temperature, for example, elemental bromine or an inorganic or organic bromine containing compound such as, respectively, sodium bromide or tetrabromoethane.

The oxidation is conducted in the stirred zone of STR 14 maintained at a temperature in the range of 360°–450° F, preferably 380°–425° F, with such pressure as is necessary for temperature control and to maintain a liquid phase in the oxidation zone. Residence time in the oxidation zone can be from 20 to 90 minutes.

Under such oxidation conditions most of the desired phthalic acid is present as high purity crystals formed in the oxidation zone as a slurry in liquid acetic acid.

Processing the fluid oxidation effluent in line 22 from STR 14 to recover the phthalic acid product according to prior techniques has been accomplished by cooling such effluent to below the boiling point of acetic acid and depressuring to atmospheric pressure while crystallizing additional product from solution thereby causing growth of crystals. Such recovery causes contamination of the growing crystals by impurities in the acetic acid mother liquor co-precipitating therefrom on the surface of the otherwise potentially available high purity crystalline product.

However, by continuously removing the fluid effluent through line 22 and pump 23 to a classification system 24–34 at or about reaction temperature and pressure wherein substantially all of the liquid portion of the reactor fluid effluent is displaced with fresh, hot acetic acid, the impurities are prevented from precipitating from the mother liquor and are displaced with it. One key operation to the present inventive process is the dual purpose classification-displacement system which displaces original mother liquor containing dissolved impurities and small phthalic acid crystals and forms a new suspension of the large crystals in hot, fresh acetic acid. Said dual purpose system should operate at a temperature not more than 50° below the oxidation zone temperature because, as has been discovered, formylbenzoic acid and toluic acid contamination of crystalline TA or IA is temperature dependent and increases rapidly at temperatures more than 50° below oxidation temperature. By displacing the original mother liquor with hot, fresh acetic acid at a temperature above the melting point of the impurities, i.e. at or about oxidation temperature, contamination of the high purity crystals is minimized.

Any means for effecting such displacement and separation can be used. For example, separation of the originally produced suspension of phthalic acid crystals can be accomplished by gravity in a settling tower, trays or decanters, or by centrifuged force in cyclones which permit separation of a substantial amount of original mother liquor as overflow and a thickened suspension of phthalic acid crystals as underflow and to which fresh solvent may or may not be added in all steps in counter- or cross-flow for mother liquor displacement. Although two step operation is conceivable, it is preferred to use at least three of such steps connected in series flow relationship to which fresh acetic acid is used in counter-flow in the last two steps, more preferably by the counter-flow addition to the last step. The most preferred system contains three series connected hydraulic cyclones (e.g. 24, 27 and 31), also known as hydroclones, into which feed enters tangentially to provide the centrifugal force and from which the heaviest or concentrate suspension of solids is discharged as underflow and lighter separated fluid is discharged as overflow.

The first hydraulic cyclone 24 of the preferred series of hydraulic cyclones is used only for solids suspension thickening by removal of a substantial proportion of the original mother liquor as overflow 25 and a provision of underflow 26 as thickened solids suspension in the remainder of the mother liquor. Part of overflow mother liquor 25 containing small phthalic acid crystals is returned to the oxidation zone through line 61 to enhance nucleation therein while the remainder of overflow stream 25 is charged via line 62 to solvent recovery as described later. Said underflow of thickened suspension of phthalic acid is charged as feed to the second hydroclone 27.

The second hydraulic cyclone 27 also receives as feed the overflow from the third or last hydraulic cyclone 31 via line 28, pump 33 and line 28a. The third overflow comprises some of the small phthalic acid crystals suspended in fresh solvent. Thus, in the second hydraulic cyclone there occurs dilution of the first step thickened suspension of phthalic acid solids in original mother liquor, washing of the phthalic acid solids by fresh solvent once used as wash liquor in the last step, thickening of the diluted suspension of phthalic acid solids, and increased displacement of original mother liquor. The fluid overflow in line 29 from the second hydraulic cyclone 27 comprising most of the remaining original mother liquor, a substantial portion of the second wash use of fresh solvent, and small phthalic acid crystals, is charged to the stirred oxidation zone of STR 14 via line 29 for enhancement of crystal growth.

The second hydraulic cyclone's underflow in line 30 is charged as part of the feed to the third hydraulic cyclone 31. Fresh, hot acetic acid charged via line 32 makes up the remainder of the feed to the third hydraulic cyclone wherein, as in the second, there occurs dilution of the thickened phthalic acid solids suspension, washing of the suspended solids, displacement of acetic acid carried from the second to the third hydraulic cyclone, removal of the remaining small phthalic acid crystals, and thickening of the suspension of phthalic acid solids. The overflow fluid in line 28 from the third hydraulic cyclone comprises fresh acetic acid wash liquor and displaced mother liquor as the liquid portion of said overflow fluid and suspended remaining small phthalic acid crystals. Such third overflow fluid is passed via line 28 through pump 33 and line 28a to the second hydraulic cyclone 27 as part of its feed as before mentioned. The third stage underflow thickened phthalic acid suspension in line 34 consists essentially of only two components which are substantially fresh acetic acid and suspended washed phthalic acid solids.

Said third underflow in line 34, at a temperature not more than 50° below that of the oxidation zone, is passed to a stirred receiving and holding zone 35 via line 34 where the thickened suspension of phthalic acid crystals is quench cooled to or below the boiling point of acetic acid at atmospheric pressure by combining it with fresh, cold acetic acid charged by line 36; e.g. acetic acid at or close to ambient temperature. The amount of cold quench solvent used will, of course, depend on the heat content of the third stage underflow in line 34 and the temperature of the cold quench solvent but otherwise the amount thereof is not critical. This feature of quench cooling with cold, fresh acetic acid is another key point of the invention. This feature prevents flashing of mother liquor adhering to the phthalic acid crystals which flashing is known to promote the contamination of the crystals with impurities. In addition, dilution of the adhering mother liquor with cold, fresh acetic acid lowers the concentration of the contaminants in the diluted mother liquor to the point where most of them remain in solution while cooling is taking place. Further cooling can be effected, if necessary, by recirculation of the slurry via line 32 by pump 38 through a heat exchanger 39 and returning it via line 40 to reslurry drum 35 rather than by solvent vaporization.

After quench cooling with fresh cold solvent, the resulting slurry is withdrawn by valved transfer line 41 to solid-liquid separation, for example, in centrifugal filter 42. The wet filter cake therein is washed with dehydrated recycle solvent entering by line 43 and discharged via solids transfer line 44 to drying. The removed solvent drawn from solid-liquid separator 42 through line 45 is collected in a drum 46 and returned to the front end of the process through line 47, pump 48 and line 12.

As previously mentioned, the portion of overflow in line 62 from the first hydraulic cyclone 24 is further processed to remove solvent. The hot, pressurized overflow is flash evaporated at one atmosphere and ambient temperature in a flash drum 49. The vapors of acetic acid solvent leave flash drum 49 via vapor transfer 50 and are charged to distillation column 52 along with the condensate in line 21 from the reactor overhead condensor 18 as mentioned earlier for recovery of acetic acid. Residue is removed from flash drum 49 through line 51. Water vapor from the column 52 is withdrawn by line 53 through heat exchanger 54, and the resulting condensate collected in condensate drum 55. Such condensate is removed therefrom through line 56, is then recycled in part as reflux in line 57 to column 52 and the remainder is removed through line 58. Recovered acetic acid is withdrawn from column 52 through line 59 and is combined with make-up fresh acetic acid from source 60 and is used in the quenching and washing steps described earlier.

EXAMPLE OF THE INVENTIVE PROCESS

The process of this invention will be illustrated according to the accompanying drawing wherein a premixed feed stream comprised of 44.2 parts p-xylene, and 0.3 parts catalyst and bromine-promoter in line 11 is mixed with 55.5 parts recycled solvent in line 12 and introduced into reactor 14 together with recycled mother liquor solvents in lines 29 and 61 at 119,130 lbs./hr. Temperature in the oxidation zone is 440° F and pressure is 220 psig. Air is supplied to the reactor through line 13 at 12,525 SCFM. Water formed in the reactor as a result of the oxidation is kept below 7.5 wt. % by removing 24,150 lbs./hr. of condensate from the secondary vent condensor pot 18 through line 21. Residence time in the reactor is 90 minutes during which time crystallization occurs. A suspension of phthalic acid crystals approximately 99.95% pure is continuously removed from the reactor in stream 22 comprising 24,130 lbs. phthalic acid, and 79,970 lbs. solvent at a rate of 104,130 lbs./hr. The suspension is at 400° F and 220 psig.

The suspension of phthalic acid crystals is charged tangentially into hydroclone 24. Overflow from hydroclone 24 containing about 8% small phthalic acid crystals is withdrawn at 69,820 lbs./hr. through transfer line 25 with 55,850 lbs./hr. being returned to the reactor through line 61 and 13,970 lbs./hr. being charged to flash drum 49 operated at atmospheric pressure. From flash drum 49 there is evaporated 9,140 lbs./hr. of mother liquor by the decrease in pressure from 220 psig to atmospheric pressure. The vapors are charged to distillation column 52 through line 50 to recover acetic acid. Residue is withdrawn for discard from flash drum 49 through line 51 at 4,830 lbs./hr.

Underflow thickened suspension from hydroclone 24 is withdrawn at 34,310 lbs./hr., 400° F, and 300 psig and diluted with overflow from hydroclone 31 through line 28 at 39,770 lbs./hr. and 400° F to make up the feed to hydroclone 27. Overflow from hydroclone 27 containing most of the remaining original mother liquor and small phthalic acid crystals is returned to the reactor at 40,000 lbs./hr. through line 29. The re-thickened suspension from the hydroclone 27 is withdrawn as underflow at 34,080 lbs./hr., 400° F, and 230 psig, and combined with fresh, hot solvent through line 32 at 35,990 lbs./hr. and 400° F to make up the feed to hydroclone 31. The underflow from hydroclone 31 is withdrawn at 30,300 lbs./hr., 400° F, and 180 psig through line 34 and is comprised of 15,150 lbs. phthalic acid crystals and 15,150 lbs. acetic acid-water solvent. The phthalic acid crystals suspended in hot, fresh solvent are of approximately 99.95% purity and are charged to stirred holding tank 35 through line 34 and quenched with 20,200 lbs. fresh acetic acid at 150° F from line 36 and cold recycle slurry from line 40. After quenching at 210° F, the suspension is depressured to atmospheric pressure and transferred through line 41 to centrifuge 42 at 50,500 lbs./hr. Centrifuge 42 separates 16,670 lbs./hr. of wet washed cake from 33,830 lbs./hr. solvent which is collected in drum 46 and recycled to the feed mixer through line 12.

The wet cake product from line 44 is dried to produce terephthalic acid of fiber-grade, containing about 60 ppm p-toluic acid and 300 ppm p-formylbenzoic acid.

What is claimed is:

1. In a process of recovering high purity isophthalic and/or terephthalic acid from the liquid effluent of the oxidation of meta and/or para dialkyl substituted benzene, said alkyl substituents having 1 to 4 carbon atoms, with molecular oxygen in an oxidation zone in the presence of an acetic acid solution of heavy metal oxidation catalyst and a source of bromine at an elevated temperature in the range of from 360° up to 450° F and a pressure in the reaction zone to maintain said solution in the liquid phase at said temperature, wherein said oxidation produces a liquid oxidation effluent comprising a suspension of said phthalic acid as crystalline product in the liquid acetic acid mother liquor solution of said catalyst components, by-product water, and aromatic impurities and a gaseous effluent comprising a mixture of nitrogen, oxides of carbon, water vapor, vaporized acetic acid, and small amounts of molecular oxygen; and wherein said gaseous effluent is cooled to condense water and solvent vapor therefrom and the condensate is returned to the oxidation zone as a means of controlling temperature in said reaction zone, the improvement which comprises:
   1. adding fresh, hot acetic acid and small phthalic acid crystals to substantially all the orginal acetic acid mother liquor portion of the oxidation effluent at a temperature of from 50° below said oxidation temperature up to said oxidation temperature to form a new suspension of large phthalic acid crystals in hot, fresh acetic acid and (b) the removal of the displaced acetic acid mother liquor and the small crystals suspended therein for recycle to the reaction zone;
   2. quenching said new suspension of crystalline phthalic acid by the addition thereto of cold, fresh acetic acid in an amount to cool the suspension to a temperature at or below the boiling point of acetic acid at atmospheric pressure;
   3. depressuring said new suspension of crystalline phthalic acid in fresh acetic acid to atmospheric pressure;
   4. separating the crystalline phthalic acid from the fresh acetic acid by means for solid-liquid separation at atmospheric pressure;
   5. recycling the separated fresh acetic acid to the reaction zone; and
   6. drying the separated crystalline product.

2. The process of claim 1, wherein said oxidation takes place at a temperature of from 380° to 425° F, the dialkylbenzene oxidized is m- or p-xylene, the catalyst metal comprise cobalt and manganese, the weight ratio of solvent to meta or paraxylene feed is in the range of 3.0 to 10.0: 1.0, and the residence time in the reaction zone being 20 to 90 minutes.

3. The process of claim 2, wherein an oxygen containing gas having 21-50 volume % oxygen is supplied to the oxidation zone to provide an oxygen content in the gaseous effluent in the range of 2 to 8 volume % oxygen on a solvent vapor-free basis.

4. The process of claim 3, wherein the water concentration in said reaction medium is kept below 12 weight % by removing a portion of said gaseous effluent condensate.

5. The process of claim 4, wherein said combination of classification and displacement is conducted in two series connected hydraulic cyclones by charging said fluid effluent to the first hydraulic cyclone from which a thickened suspension of crystalline phthalic acid flows as underflow and a substantial portion of the liquid acetic acid mother liquor flows as overflow, said thickened suspension is fed to the second hydraulic cyclone together with the hot fresh acetic acid and a portion of the overflow from the first hydraulic cyclone, wherein the second hydraulic cyclone produces (a) an overflow containing small phthalic acid product for recycle back to the reaction zone and (b) an underflow comprising re-thickened crystalline phthalic acid suspended in fresh, hot acetic acid as feed for the quenching step.

6. The process of claim 5 wherein the combination classification and displacement is conducted by charging the fluid effluent to the first of three hydraulic cyclone crystal classification and acetic acid mother liquor displacement zones interconnected for series flow therethrough wherein each of which forms a thickened suspension of crystals as an underflow and a liquid containing displaced acetic acid mother liquor as overflow, the underflow thickened suspension from the first zone and the overflow from the third zone are combined to dilute such underflow, the diluted suspension is fed to the second zone, a portion of the overflow from the first zone and the entire overflow from the second zone containing the small crystals of phthalic acid are combined and fed to the oxidation zone, the underflow re-thickened suspension underflow from the second zone is combined with fresh, hot acetic acid to dilute the re-thickened suspension, the diluted re-thickened suspension is fed to the third zone, and the new thickened suspension of large crystals of the phthalic acid product underflow from the third zone is fed to the quenching step.

7. The process of claim 6 wherein said new suspension of large crystalline phthalic acid is charged to a re-slurrying zone operated at the oxidation zone pressure and at a temperature of about the oxidation reaction temperature and quenched and depressured therein by diluting said new suspension with a spray of fresh acetic acid in an amount sufficient to retain the impurities in solution at atmospheric pressure at or below the boiling point of the fresh solvent.

* * * * *